US010875936B2

(12) United States Patent
Torri et al.

(10) Patent No.: US 10,875,936 B2
(45) Date of Patent: Dec. 29, 2020

(54) DERIVATIVES OF N-DESULFATED GLYCOSAMINOGLYCANS AND USE AS DRUGS

(71) Applicant: Novahealth Biosystems, LLC, Waunakee, WI (US)

(72) Inventors: Giangiacomo Torri, Milan (IT); Annamaria Naggi, Legnano (IT)

(73) Assignee: Novahealth Biosystems, LLC, Waunakee, WI (US)

( * ) Notice: Subject to any disclaimer, the term of this patent is extended or adjusted under 35 U.S.C. 154(b) by 0 days.

(21) Appl. No.: 15/032,248

(22) PCT Filed: Oct. 23, 2014

(86) PCT No.: PCT/EP2014/072707
§ 371 (c)(1),
(2) Date: Apr. 26, 2016

(87) PCT Pub. No.: WO2015/062951
PCT Pub. Date: May 7, 2015

(65) Prior Publication Data
US 2016/0237178 A1    Aug. 18, 2016

(30) Foreign Application Priority Data
Oct. 31, 2013 (IT) .............................. LO2013A0005

(51) Int. Cl.
| C08B 37/00 | (2006.01) |
| A61K 31/727 | (2006.01) |
| A61K 31/726 | (2006.01) |
| A61K 31/728 | (2006.01) |
| A61K 31/737 | (2006.01) |
| C08B 37/08 | (2006.01) |

(52) U.S. Cl.
CPC ........ *C08B 37/0075* (2013.01); *A61K 31/726* (2013.01); *A61K 31/727* (2013.01); *A61K 31/728* (2013.01); *A61K 31/737* (2013.01); *C08B 37/0063* (2013.01); *C08B 37/0069* (2013.01); *C08B 37/0072* (2013.01); *C08B 37/0078* (2013.01)

(58) Field of Classification Search
CPC ............ C08B 37/0075; C08B 37/0078; A61K 31/727
USPC ........................................................ 536/21
See application file for complete search history.

(56) References Cited

U.S. PATENT DOCUMENTS

| 5,250,519 A * | 10/1993 | Conrad ................. A61K 31/715 514/56 |
| 5,296,471 A * | 3/1994 | Holme .................. A61K 31/715 514/54 |
| 5,583,121 A * | 12/1996 | Chaudry .............. A61K 31/715 514/56 |
| 2011/0200673 A1 | 8/2011 | Mousa | |

FOREIGN PATENT DOCUMENTS

| CN | 1547477 A | 11/2004 |
| CN | 1327795 A | 12/2011 |
| CN | 102924627 A | 2/2013 |
| JP | 4-502928 A | 5/1992 |
| JP | 2005506326 A | 3/2005 |
| WO | WO 90/04607 A2 | 5/1990 |
| WO | WO 92/17188 A1 | 10/1992 |
| WO | WO 01/55221 A1 | 8/2001 |
| WO | WO 03/022291 A1 | 3/2003 |

OTHER PUBLICATIONS

Bjornsson et al. (The Journal of Pharmacology and Experimental Therapeutics, vol. 245, No. 3, 804-808).*
Fransson et al.; Relationship between anticoagulant activity of heparin and susceptibility to periodate oxidation; Jan. 1, 1979; pp. 119-123; FEBS Letters, Elsevier, Amsterdam, NL, vol. 97, No. 1.
Wang yu et al.; China Drug Inspection Series—Drug inspection, the 1st edition; China Medical Science Press; Oct. 31, 2011; 4 pages.
Annamaria Naggi et al., "Modulation of the heparanase-inhibiting activity of heparin through selective desulfation, graded N-acetylation, and glycol splitting"; the Journal of Biological Chemistry, vol. 280, No. 13, p. 12103-12113, Jan. 12, 2005.
Benito Casu et al., "Undersulfated and glycol-split heparins endowed with antiangiogenic activity"; J. Med. Chem., vol. 47, p. 838-848, Jan. 8, 2004.
Claudio Pisano et al., "Undersulfated, low-molecular-weight glycol-split heparin as an antiangiogenic VEGF antagonist"; Glycobiology, vol. 15, No. 2, p. 1C-6C, Oct. 20, 2004.
(Continued)

*Primary Examiner* — Shaojia A Jiang
*Assistant Examiner* — Michael C Henry
(74) *Attorney, Agent, or Firm* — Reinhart Boerner Van Deuren P.C.

(57) ABSTRACT

The invention relates to N-desulfated and optionally 2-O-desulfated glycosaminoglycan derivatives, wherein at least part of the adjacent diols and OH/NH$_2$ have been converted into the corresponding aldehyde, which aldehydes have been then reduced to the corresponding alcohol. These products are endowed with heparanase inhibitory activity and anti-tumor activity. Said glycosaminoglycan derivatives are obtained from natural or synthetic glycosaminoglycan, preferably from unfractionated heparin, low molecular weight heparins (LMWHs), heparan sulfate or derivatives thereof. The invention further relates to the process for preparation of the same and further to their use as active ingredients of medicaments, also in combination with known established drugs or treatments. The present invention further relates to a process for breaking the $C_2$-$C_3$ linkage of glucosamine residues of a glycosaminoglycan by oxidation of said glycosaminoglycan.

4 Claims, 1 Drawing Sheet

(56) References Cited

OTHER PUBLICATIONS

Graham-Rowe, D., Multiple Myeloma Outlook, Nature, Dec. 15, 2011, pp. S34-S35, vol. 480.
Fux, Liat et al., Heparanase: Busy at the cell surface, Trends Biochem Sci., Oct. 2009, pp. 511-519, vol. 10.
Sanderson, Ralph et al., Syndecan-1: A dynamic regulator of myeloma microenvironment, Clin Exp Metastasis, 2008, pp. 149-159, vol. 25.
Ilan, Neta et al., Regulation, function and clinical significance of heparanase in cancer metastasis and angiogenesis, Science Direct: The International Journal of Biochemistry & Cell Biology, 2006, pp. 2018-2039, vol. 38.
Casu, Benito et al., Non-Anticoagulant Heparins and Inhibition of Cancer, Pathophysiology of Haemostasis and Thrombosis, Aug. 2007, pp. 195-203, vol. 36.
Vlodavsky, Israel et al., Haparanase: Structure, Biological Functions, and Inhibition by Heparin-Derived Mimetics of Heparan Sulfate, Current Pharmaceutical Design, 2007, pp. 2057-2073, vol. 13.
Naggi, Annamaria et al., Modulation of the Heparanase-inhibiting Activity of Heparin through Selective Desulfation, Graded N-Acetylation, and Glycol Splitting, JBC Papers in Press, Jan. 12, 2005, pp. 12103-12113, vol. 280.
Casu, Benito et al., Structure and Active Domains of Heparin, Chemistry and Biology of Heparin and Heparan Sulfate, 2005, pp. 1-28, Elsevier Ltd.
Casu, Benito et al., Structure and biological interactions of heparin and heparan sulfate, Advances in Carbohydrate Chemistry and Biochemistry, 2001, pp. 159-206, vol. 57, Academic Press, an Elsevier Science Imprint.
Zacharski, L.R. et al, Heparin as an anticancer therapeutic, Expert Opinion on Investigational Drugs, Jul. 2008, pp. 1029-1037, vol. 17, London, UK.
Yang, Yang et al., The syndecan-1 heparan sulfate proteoglycan is a viable target for myeloma therapy, Blood, Sep. 15, 2007, pp. 2041-2048, vol. 110 No. 6, the American Society of Hematology.
Naggi, Annamaria et al., Glycol-Splitting as a Device for Modulating Inhibition of Growth Factors and Heparanase by Heparin and Heparin Derivatives, Chemistry and Biology of Heparin and Heparan Sulfate, 2005, pp. 461-481, Elsevier Ltd., Amsterdam.
Chemical Abstract Registry No. 53260-52-9; Nov. 16, 1984.
Chen, Jin-Lian et al., Effect of non-anticoagulant N-Desulfated heparin on expression of vascular endothelial growth factor, angiogenesis and metastasis of orthotopic implantation of human gastric carcinoma, World Journal of Gastroenterology, Jan. 21, 2007, pp. 457-461, vol. 13, the WJG Press.
Zhou, Tong et al., Effect of N-desulfated heparin on hepatic/renal ischemia reperfusion injury in rats, World Journal of Gastroenterology, 2002, pp. 897-900, vol. 8, the WJG Press.
Naggi, Annamaria et al., Toward a Biotechnological Heparin through Combined Chemical and Enzymatic Modification of the *Escherichia coli* K5 Polysaccharide, Seminars in Thrombosis and Hemostasis, Oct. 2001, pp. 437-443, vol. 27, No. 5, Thieme Medical Publishers, Inc., New York.
Inoue, Yuko et al., Selective N-Desulfation of Heparin with Dimethyl Sulfoxide Containing Water or Methanol, Carbohydrate Research, 1976, pp. 87-95, vol. 46, Elsevier Scientific Publishing Company, Amstrerdam—Belgium.
Naggi, Annamaria et al., Generation of anti-factor Xa active, 3-O-sulfated glucosamine-rich sequences by controlled desulfation of oversulfated heparins, Carbohydrate Research, Dec. 7, 2001, pp. 283-290, vol. 336 No. 4, Elsevier Science Ltd.
Rej Rabindra N. et al., Base-catalyzed conversation of the a-L-iduronic acid 2-sulfate unit of heparin into a unit of a-L-galacturonic acid, and related reactions, Carbohydrate Research, Apr. 25, 1990, pp. 437-447, vol. 200, Elsevier Science Publishers B.V., Amsterdam—Netherlands.
Casu, Benito et al., Undersulfated and Glycol-Split Heparins Endowed with Antiangiogenic Activity, Journal of Medicinal Chemistry, Feb. 12, 2004, pp. 838-848, vol. 47 No. 4, American Chemical Society, Washington D.C.
Bisio, Antonella et al., High-Performance Liquid Chromatographic/Mass Spectrometric Studies on the Susceptibility of Heparin Species to Cleavage by Heparanase, Seminars in Thrombosis and Hemostasis, Jul. 2007, pp. 488-495, vol. 33, No. 5, Thieme Medical Publishers, Inc. New York.
Hammond, Edward et al., Development of a colorimetric assay for heparanase activity suitable for kinetic analysis and inhibitor screening, Analytical Biochemistry, Jan. 1, 2010, pp. 112-116, vol. 396 Issue 1, Elsevier.
Vlodavsky, Israel et al., Current Protocols in Cell Biology, 1999, pp. 1-11, vol. 1, John Wiley & Sons, Inc., United States of America.
Naggi, Annamaria, et al. "Modulation of the heparanase-inhibiting activity of heparin through selective desulfation, graded N-acetylation, and glycol splitting." Journal of Biological Chemistry 280.13 (2005): 12103-12113.†

* cited by examiner
† cited by third party

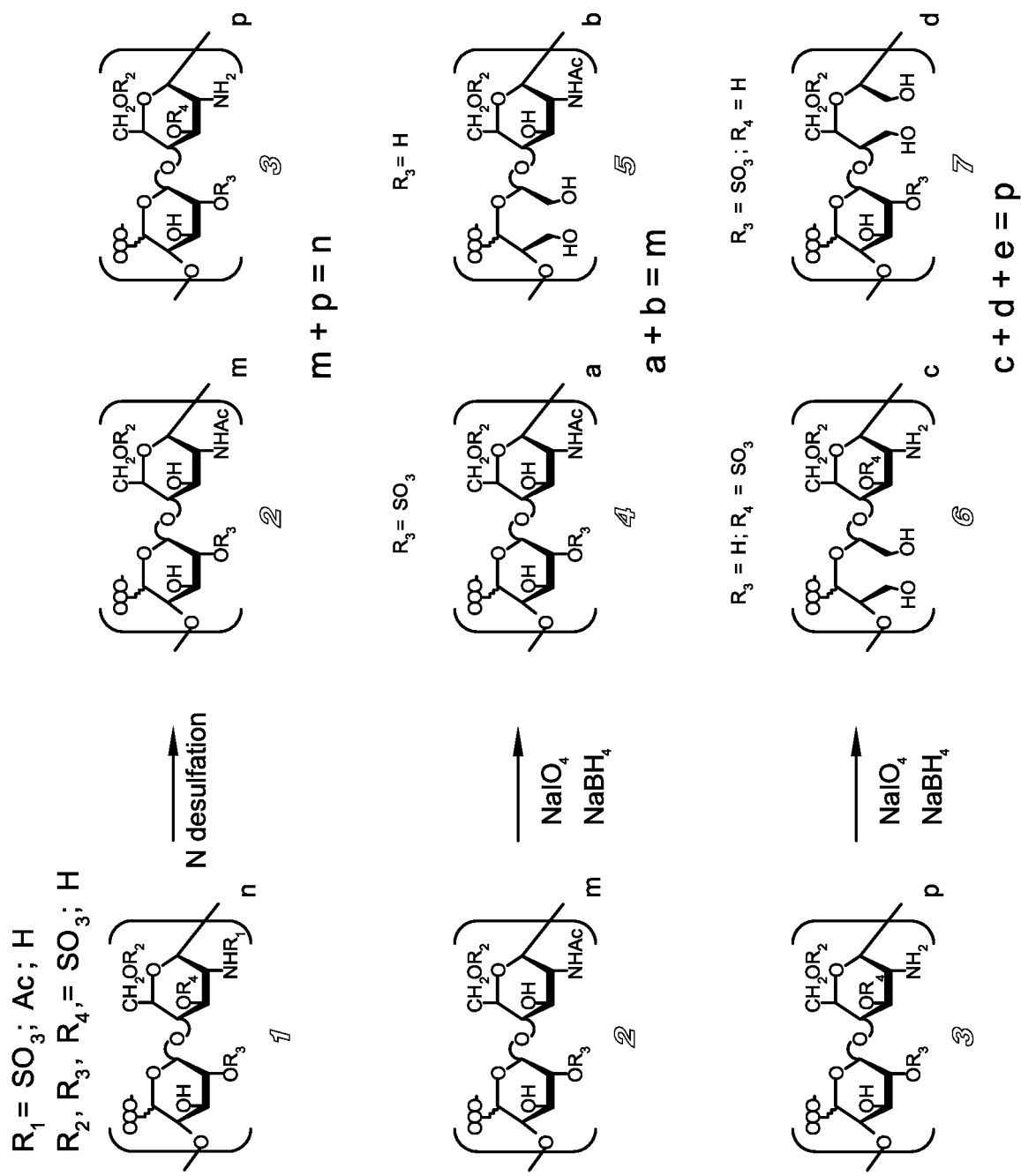

DERIVATIVES OF N-DESULFATED GLYCOSAMINOGLYCANS AND USE AS DRUGS

CROSS-REFERENCE TO RELATED APPLICATION

This Application is a 35 USC § 371 US National Stage filing of International Application No. PCT/EP2014/072707 filed on Oct. 23, 2014, and claims priority under the Paris Convention to Italian Patent Application No. LO2013A000005 filed on Oct. 23, 2013.

FIELD OF THE DISCLOSURE

SUMMARY

The invention relates to N-desulfated and optionally 2-O-desulfated glycosaminoglycan derivatives, wherein at least part of the adjacent diols and OH/NH$_2$ have been converted into the corresponding aldehyde, which aldehydes have been then reduced to the corresponding alcohol. These products are endowed with heparanase inhibitory activity and anti-tumor activity. Said glycosaminoglycan derivatives are obtained from natural or synthetic glycosaminoglycan, preferably from unfractionated heparin, low molecular weight heparins (LMWHs), heparan sulfate or derivatives thereof. Natural glycosaminoglycans can be obtained from any animal source (different animal species and organs can be employed).

The invention further relates to the process for preparation of the same and further to their use as active ingredients of medicaments, useful in pathological conditions.
In particular, said pathological conditions comprise multiple myeloma and other cancers (i.e. sarcomas, carcinomas, hematological malignancies), including their metastatic form. The glycosaminoglycan derivatives of the invention can be used as medicaments also in combination with other therapies, either oncological therapies or not. Furthermore, the invention relates to the use of said N-desulfated and optionally 2-O-desulfated glycosaminoglycan derivatives, preferably obtained from heparins and low molecular weight heparins (LMWHs), in any therapeutic indication gaining benefit from the inhibition of heparanase (i.e. diabetic nephropathy, inflammatory bowel disease, colitis, arthritis, psoriasis, sepsis, atherosclerosis), also in combination with known established drugs or treatments.

The invention also relates to pharmaceutical compositions containing as active ingredient at least one of said N-desulfated and optionally 0-desulfated glycosaminoglycan derivatives, wherein at least part of the adjacent diols and OH/NH$_2$ have been converted into the corresponding aldehyde, followed by reduction to the corresponding alcohol. Optionally the invention relates to pharmaceutical compositions containing as active ingredient at least one of said glycosaminoglycan derivatives in combination with at least one other active ingredient, more preferably a therapeutic compound. Preferably, said glycosaminoglycan derivatives are heparin derivatives or low molecular weight heparins (LMWHs).

BACKGROUND OF THE DISCLOSURE

Multiple myeloma is the second most prevalent hematologic malignancy and accounts for over 10% of all hematologic cancer in Unites States, with around 20,000 new cases each year and mortality higher than 50% (Graham-Rowe D., 2011, Multiple myeloma outlook. Nature 480, s34-s35).

Over the last few years, promising therapies have been developed, such as the administration of proteasome inhibitor (Velcade), bisphosphonates, thalidomide and others. The effectiveness of these agents is, at least in part, due to their impact on the myeloma tumor microenvironment.

Although efficacy against myeloma has been shown by said agents, there is need for new and improved drugs for treating myeloma and other tumors.

Heparanase is an endo-β-glucuronidase that cleaves the heparan sulfate (HS) chains of proteoglycans (PG-HS), such as syndecan-1, thereby releasing HS-bound growth factors.

In humans, there appears to be a single dominant functional heparanase enzyme capable of cleaving HS. Heparanase is expressed by many human tumors, where it significantly increases both the angiogenic and the metastatic potential of tumor cells. Elevated heparanase levels have been in fact correlated with advanced progression and metastasis of many tumor types. For example, high level of heparanase is associated with a shorter post-operative survival time of patients. A direct role of heparanase in tumor metastasis has been demonstrated in Prof.s Vlodaysky's and Sanderson's laboratories, where our novel inhibitors have been tested.

In addition to its enzymatic functions, that include release of HS-bound growth factors and degradation of the extracellular matrix (ECM) by invasive cells, heparanase has also a non-enzymatic function that may impact tumor behavior and its microenvironment. Sanderson's group pioneered the study of heparanase and syndecan-1 in myeloma, establishing that heparanase acts as a master regulator of its aggressive tumor phenotype. This occurs by promoting the up-regulation of VEGF and MMP-9, that together stimulate tumor growth, metastatic and osteolytic bone destruction. It was in fact demonstrated in vivo that heparanase promotes the growth of myeloma tumors and spontaneous metastasis to bone and that heparanase expression by tumor cells fuels rampant osteolysis, at least partially due to up-regulation of RANKL expression. The osteolysis promoting effect of heparanase may be of great importance because bone-bound growth factors are released when bone is degraded. In addition, osteoclasts can release tumor growth promoting factors, such as HGF. Together these factors may help establish niches within the bone marrow that support tumor cell homing and subsequent growth (Fux, L., et al. 2009, Heparanase: busy at the cell surface. Trends Biochem Sci 34 (10): 511-519; Sanderson R. D., and Yang Y., 2008, Syndecan-1: a dynamic regulator of the myeloma microenvironment. Clin. Exp Metastasis 25:149-59; Ilan N., et al. 2006. Regulation, function and clinical significance of heparanase in cancer metastasis and angiogenesis. Int. J. Biochem. Cell Biol. 38: 2018-2039). Inhibition of heparanase is thus a feasible target of myeloma therapy, supported by the fact that there is a single enzymatically active heparanase and by the fact that its expression in normal tissues is rare. Furthermore, it has been shown that heparanase knock-out mice are viable and exhibit no visible disorders. This indicates that little or no side effect can derive from a heparanase inhibition strategy (Casu B., et al. 2008. Non-anticoagulant heparins and inhibition of cancer. Pathophysiol Haemost Thromb. 36: 195-203; Vlodaysky I., et al. 2007. Heparanase: structure, biological functions, and inhibition by heparin-derived mimetics of heparan sulfate. Curr Pharm Des. 13: 2057-2073; Naggi A., et al. 2005. Modulation of the Heparanase-inhibiting Activity of Heparin through Selective Desulfation, Graded N-Acetylation, and Glycol Splitting. J. Biol. Chem. 280: 12103-12113).

Heparin is a linear polydisperse sulfated polysaccharide of the glycosaminoglycan family, endowed with anticoagulant and antithrombotic activity. The saccharidic chains of heparin consist of alternating uronic acid and D-glucosamine residues. The major repeating unit is the disaccharide 2-O-sulfated L-iduronic acid (IdoA2S)α(1→4) and N-, 6-O-sulfated D-glucosamine (GlcN6S). Minor constituents are non-sulfated L-iduronic and D-glucuronic acid, along with N-acetyl D-glucosamine and N-, 3-O-, 6-O-trisulfated D-glucosamine (Casu B., 2005. Structure and active domains of heparin. In: Chemistry and Biology of Heparin and Heparan Sulfate. Amsterdam: Elsevier. 1-28; Casu B. and Lindahl U. 2001, Structure and biological interactions of heparin and heparan sulfate. Adv Carbohydr Chem Biochem 57: 159-206). Heparin, which is structurally similar to HS, is capable of efficiently inhibiting heparanase, but its use at high doses, in a heparanase inhibition strategy, is impossible due to its anticoagulant activity.

Interestingly, low molecular weight heparins (LMWHs), which are more bioavailable and less anticoagulant than heparin, appear to prolong survival of cancer patients, probably through direct effect on tumor growth and metastasis. This may be due, at least in part, to inhibition of heparanase enzymatic activity (Zacharski L. R., and Lee, A. Y. 2008, Heparin as an anticancer therapeutic. Expert Opin Investig Drugs 17:1029-1037; Yang Y et al., 2007, The syndecan-1 heparan sulfate proteoglycan is a viable target for myeloma therapy. Blood 110:2041-2048).

Effective inhibitors of the enzymatic activity of heparanase have been selected in the prior art by studying heparanase inhibition by non-anticoagulant heparins, most of which contain non sulfated uronic acid residues modified by opening of the glucosidic ring at 2-3 bond (glycol splitting). Said inhibitors differ in their degree of O-sulfation, N-acetylation and glycol splitting of non-sulfated uronic acid residues both pre-existing and generated by graded 2-O-desulfation (Naggi A., 2005. Glycol-splitting as a device for modulating inhibition of growth factors and heparanase inhibition by heparin and heparin derivative. In: Chemistry and Biology of Heparin and Heparan Sulfate. Amsterdam: Elsevier 461-481).

The term "glycol split" (gs) conventionally refers to carbohydrate polymers that present opening of some monosaccharide residues due to the break (glycol splitting) of one linkage between two adjacent carbons, each bearing a hydroxyl group. The first generation glycol split heparins, i.e. the so-called "reduced oxyheparins" (RO-heparins), largely consisted of unmodified polysulfated blocks occasionally interrupted by glycol split residues corresponding to non sulfated glucuronic acid/iduronic acid residues that were present along the original chains (Naggi A., 2005. Glycol-splitting as a device for modulating inhibition of growth factors and heparanase inhibition by heparin and heparin derivative. In: Chemistry and Biology of Heparin and Heparan Sulfate. Amsterdam: Elsevier 461-481). This chemical action on heparin, modifying the glucuronic acid residues within the binding site of ATIII, reduces or abolishes its anticoagulant activity, making it possible to use it at high doses.

WO 92/17188 discloses anti-proliferative activity, with respect to smooth muscle cells, of a non-anticoagulant species of heparin. Said heparin is prepared by N-deacetylation of the N-acetyl glucosamine units, which are a minor component of natural heparin's chains, with a hydrazine-containing agent, followed by periodate oxidation of diols or adjacent OH/$NH_2$ groups to the corresponding aldehydes. The oxidation is followed by reduction of aldehydes to alcohols, without substantial fragmentation of the glycosaminoglycan. The N-sulfated units are unaffected by the oxidation-reduction.

N-desulfated heparins (Chemical Abstract Registry number 53260-52-9), also known as "heparamine" in the Merck index (14$^{th}$ Editor, 2006), are known to be endowed with several effects: a reduced anticoagulant activity, some activity against metastasis of gastric cancer in mice, by inhibiting VEGF expression and angiogenesis (Chen-J-L et al. 2007, World J. Gastroenterol 21, 457-461) and prevention of hepatic/renal damage induced by ischemia and reperfusion (Chen-J-L et al. 2002, World J. Gastroenterol 8, 897-900). N-desulfated heparins are also known as intermediates for the synthesis of various N-acylated heparins. The degree of N-desulfation can range from 10% up to 100% of N-sulfated glucosamine residues present in heparins (Huang L. and Kerns R. J. 2006, Bioorg. Med Chem, 14, 2300-2313).

WO 01/55221 discloses glycosaminoglycans with a 2-O-desulfation degree not greater than 60% of the total uronic acid units. Said glycosaminoglycans are devoid of anticoagulant activity and show antiangiogenic activity based on the inhibition of FGF. No activity is foreseen for inhibition of heparanase.

US 2008/0051567 discloses a compound corresponding to 100% N-acetylated and 25% glycol split heparin, exerting little or no anticoagulant activity and low release of growth factors from the extracellular matrix, while inhibiting heparanase, tumor growth, angiogenesis and inflammation in experimental animal models, including Sanderson's model of myeloma.

Nevertheless, the need remains for providing improved compounds with higher heparanase inhibition activity, higher selectivity, improved bioavailability and efficacy for treating heparanase-related pathologies, such as myeloma and other tumors.

BRIEF DESCRIPTION OF THE DRAWINGS

FIG. 1: prevalent structures generated by periodate oxidation and borohydride reduction of a glycosaminoglycan.

(1) disaccharidic unit of a glycosaminoglycan polymer comprising one uronic acid (iduronic and/or glucuronic) and one glucosamine (2-N-acetylated, 2-N-unsubstituted and/or 2-N-sulfated), in which the hydroxyl group ($R_4$) can be substituted by a sulphate group or non-substituted. After N-desulfation, glycosaminoglycan polymers can comprise disaccharidic units comprising 2-N-acetylated glucosamines (2) and 2-$NH_2$ glucosamines (natural and/or N-desulfated) (3). Periodate oxidation and borohydride reduction lead to the conversion of adjacent diols of 2-O-non-sulfated uronic acid residues (5, 6, 8) and adjacent OH/$NH_2$ groups of 2-N- and 3-O-non-sulfated glucosamine (7, 8) to the corresponding aldehydes (by oxidation) and then to the corresponding alcohols (by reduction). Note that in disaccharide units containing a of N-desulfated glucosamine and a 2-O-non-sulphate uronic acid both residues are converted to dialdehydes and then to glycol split residues (8).

DETAILED DESCRIPTION OF THE DISCLOSURE

The present invention relates to novel chemically modified glycosaminoglycans, in particular heparin and LMWHs, which strongly inhibit heparanase and its heparan sulfate degrading activity.

The novel compounds of the present invention, endowed with heparanase inhibitory activity, are derivatives of N-desulfated and optionally 2-O-desulfated glycosaminoglycans, in which at least part of the adjacent diols and $OH/NH_2$ have been converted into the corresponding aldehyde, which aldehydes have been then reduced to the corresponding alcohol. The conversion to aldehydes is preferably carried out employing periodate, in conditions suitable for breaking both the linkage of adjacent diols of uronic acid residues and the $C_2$-$C_3$ linkage of glucosamine, bearing respectively the amine and hydroxyl substituents. The starting compounds can also contain naturally 2-O-non-sulfated uronic acid residues. In particular, N-desulfation occurs on the N-sulfated glucosamine residues, while 0-desulfation is on 2-O-sulfated uronic acid residues.

Preferably, the glycosaminoglycan derivatives of the present invention originate from natural or synthetic glycosaminoglycans, the latter being chemically or enzymatically prepared (Naggi A. et al., 2001, "Toward a biotechnological heparin through combined chemical and enzymatic modification of the *Escherichia coli* K5 polysaccharide. "Seminars in thrombosis and hemostasis, 27, 5437), such as unfractionated heparins, low molecular weight heparins (LMWHs), heparan sulfates or fractions thereof; more preferably the glycosaminoglycan derivatives derive from natural or synthetic heparins or LMWHs.

Specific N-desulfation of N-sulfated glucosamine residues substantially makes said residues susceptible to conversion to corresponding aldehydes (and then to corresponding alcohols), provided that these residues are also 3-O-non-sulfated. In FIG. 1 all the disaccharidic units that can be present in a glycosaminoglycan chain and their change after N-desulfation, oxidation and reduction reaction, are shown in a schematic view.

As an example, heparin chains can naturally comprise from about 5% to about 35% of 2-O-non-sulfated uronic acid residues, from 0% to 50% of N-acetylated glucosamine residues and from about 0% to 6% of N-unsubstituted (neither N-sulfated, nor N-acetylated) glucosamine residues. Different compositions depend on the heparin source (animal species, organ sources) and on the extraction procedures.

Every non-sulfated residue, both on carbon 2 and carbon 3, of a glycosaminoglycan is susceptible of conversion to aldehyde. Consequently, the extensive N-desulfation comprised in the process of the present invention provides further residues susceptible of said conversion over the percentage of susceptible units in natural glycosaminoglycans, with an increase in the percentage of units in which adjacent $OH/NH_2$ are converted to the corresponding aldehydes (and then to the corresponding alcohols), however preserving the natural content of 2-O-sulfated iduronic acid residues. Optionally, chemically induced 2-O-desulfation of glycosaminoglycans allows to modulate the ratio of glucosamine and uronic acid susceptible to the oxidation and reduction reactions according to the present invention.

The invention further relates to said glycosaminoglycan derivatives N- and optionally 2-O-desulfated, in which adjacent diols and $OH/NH_2$ have been converted into the corresponding aldehyde, with opening of the ring, which aldehydes have been then reduced to the corresponding alcohol. The invention further relates to a process for preparing said glycosaminoglycan derivatives and also to their use as active ingredients of medicaments for treating pathological conditions such as multiple myeloma and other cancers, including their metastatic forms. Furthermore, the invention relates to the use of said glycosaminoglycan derivatives in any therapeutic indication gaining benefit from the inhibition of heparanase. The invention also relates to pharmaceutical compositions containing said N-desulfated and optionally 2-O-desulfated glycosaminoglycan derivatives, in which adjacent diols and $OH/NH_2$ have been converted into the corresponding aldehyde, with opening of the ring, which aldehydes have been then reduced to the corresponding alcohol.

The N- and optionally 2-O-desulfated glycosaminoglycan derivatives of the present invention are obtainable by a process comprising:

a) N-desulfation of from 25 to 100%, preferably of from 30% to 90%, more preferably of from 45% to 80% of N-sulfated glucosamine residues of a glycosaminoglycan; optionally the process further comprises 2-O-desulfation up to 50%, preferably up to 25%, of 2-O sulfated residues of a glycosaminoglycan; the obtained product preferably comprises from 0% to 50% of N-acetylated glucosamine residues, from 50% to 100% of N-non-sulfated glucosamine residues;

b) conversion into the corresponding aldehydes, preferably by periodate oxidation, of the adjacent $OH/NH_2$ of 2N-, 3-O-non sulfated glucosamine residues and of adjacent diols of 2-O-non-sulfated uronic acid residues (chemically desulfated as well as the naturally present non-sulfated ones along the original chain); the 2N-, 3-O-non sulfated glucosamine residues can be present as from 25% to 100% c) reduction of said aldehydes, preferably by sodium borohydride, into the corresponding alcohols.

Optionally, the process further comprises partial or total deacetylation of N-acetylated residues of the glycosaminoglycan.

In preferred embodiments, the glycosaminoglycan derivatives of the present invention are obtained from natural or synthetic (chemically or enzymatically prepared) glycosaminoglycans, preferably from unfractionated heparins, LMWHs, heparan sulfate or derivatives thereof. More preferably, the glycosaminoglycan derivatives of the present invention are obtained from heparins or LMWHs.

In a preferred embodiment, the oxidation, preferably periodate oxidation, is performed under conditions to cleave both the vicinal diols of uronic acids and the bond between the $C_2$ and $C_3$ of glucosamine, bearing respectively amino and hydroxyl substituents.

In a preferred embodiment, modified glycosaminoglycan samples, preferably modified heparin or LMWH, endowed with different degrees of N-desulfation, are subjected to periodate oxidation and sodium borohydride reduction in aqueous media, performed by modification of known methods. Periodate oxidation may be performed in the presence of NTA (nitrilotriacetic acid), a chelating and sequestering agent used to reduce depolymerization, in the presence of $NaHCO_3$ or pyridine to alkalinize the solution, or in the presence of $MnCl_2$ with or without NTA. Preferably, periodate oxidation is performed in the presence of NTA. Preferably, oxidation is performed at pH comprised between 5.5 and 10.0, more preferably comprised between 6.0 and 9.0.

The present invention further relates to a process for breaking the $C_2$-$C_3$ linkage of glucosamine residues of a glycosaminoglycan, comprising: oxidation, preferably by periodate, at a pH comprised between 5.5 and 10, more preferably between 6.0 and 9.0, of said glycosaminoglycan.

Preferably, the glucosamine residues in which adjacent $OH/NH_2$ have been converted into the corresponding aldehyde, which aldehydes are then reduced to the corresponding alcohols, are from 25% to 100%, more preferably from 50% to 100%, most preferably from 60% to 90%, of the glucosamine residues of the glycosaminoglycan.

The glycosaminoglycan derived compounds obtainable by the process above preferably have a molecular weight of from 800 to 30,000 Da, depending on the process conditions and on the starting glycosaminoglycan. When unfractionated heparin is employed as starting material, the glycosaminoglycan derived compounds obtainable by the process above preferably have a molecular weight of from 3,000 to 20,000 Da, preferably from 4,000 to 12,000 Da.

The novel glycosaminoglycan derivatives of the present invention have unexpectedly shown to be strong heparanase inhibitors in vitro and to inhibit myeloma in animal models.

The products with the higher number of units wherein the adjacent diols and $OH/NH_2$ have been converted to the corresponding aldehydes, which aldehydes have been then reduced to the corresponding alcohols, are also less sulfated with respect to the natural glycosaminoglycans and to their RO derivatives. Therefore, it is expected that they display less protein interactions and more favourable pharmacokinetics than their analogues with lower contents of modified residues.

The present invention further relates to the compounds obtainable by the processes described above for use as medicaments.

In particular, the present invention relates to the compounds obtainable by the processes described above for use as antimetastatic agents, as antitumor, preferably as antimyeloma.

Heparin and low molecular weight heparin derivatives prepared according to the present invention, in spite of their low sulfation degree, have shown effective inhibition of heparanase activity, both in vitro and in vivo, in a multiple myeloma experimental model.

Furthermore, the derivatives of the present invention have shown, even at low molecular weights (see examples 5, 6 and 8), heparanase inhibitory activity higher than that of RO heparins obtained from 2-O-desulfated heparins of similar molecular weight. The latters are show in table 1.

TABLE 1

| Sample | % of glycol split uronic acids | Average molecular weight, MW (kDa) | Heparanase inhibition $IC_{50}$ (ng/ml) |
|---|---|---|---|
| RO 1 Heparin | 28 | 17 | 8 |
| RO 2 Heparin | 26 | 10 | 50 |
| RO 3 Heparin | 23 | 7 | 500 |
| RO 4 Heparin | 23 | 5 | 750 |

Data show a general trend to reduced heparanase inhibiting activity with the lowering of the molecular weight of glycol split heparin of RO type.

EXAMPLES

Compounds Preparation

N-desulfation of unfractionated heparin (hereinafter UFH) disclosed in the following examples was performed by modification of known methods (Inoue Y and Nagasawa K 1976. "Selective N-desulfation of heparin with dimethyl sulfoxide containing water or methanol." Carbohydr Res 46 (1) 87-95). The degree of N-desulfation was determined by $^{13}$C-NMR (Naggi A., et al. 2001, "Generation of anti-factor Xa active, 3-O-sulfated glucosamine-rich sequences by controlled desulfation of oversulfated heparins." Carbohydr. Res. 336, 4, 283-290).

Samples of modified heparins, endowed with different degree of N-desulfation, were subjected to periodate oxidation to give split units with two aldehyde groups and sodium borohydride ($NaBH_4$) reduction in aqueous medium to give final heparin derivatives; both reactions were performed by modification of known methods. Periodate oxidation was preferably performed in the presence of $NaHCO_3$, pyridine, $MnCl_2$ or $MnCl_2$ with NTA. Graded 2-O-desulfation of UFH was performed following modification of known methods (Jaseja M. et al. 1989 "Novel regio- and stereo-selective modifications of heparin in alkaline solution. Nuclear magnetic resonance spectroscopic evidence." Canad. J. Chem., 67, 1449-1455; R. N. Rej Arthur S. Perlin 1990 "Base-catalyzed conversion of the α-L-iduronic acid 2-sulfate unit of heparin into a unit of α-L-galacturonic acid, and related reactions." Carbohydr. Res. 200, 25, 437-447; Casu B. et al. 2004 "Undersulfated and Glycol-Split Heparins Endowed with Antiangiogenic Activity." J. Med. Chem., 47, 838-848). Hereafter "RO" indicates the % of glycol split residues in which adjacent diols and $OH/NH_2$ have been converted into the corresponding aldehyde and then into the corresponding alcohols, over the total glycosaminoglycan residues.

In Vitro Testing

Based on previous studies of Bisio et al. (Bisio A. et al. 2007 "High-performance liquid chromatographic/mass spectrometric studies on the susceptibility of heparin specie to cleavage by heparanase." Sem Thromb hemost 33 488-495), heparanase inhibiting activity was determined in vitro by the group of Prof. Vlodaysky at the University of Haifa, Israel, according to the method described by Hammond et al. (Hammond et al. 2010 "Development of a colorimetric assay for heparanase activity suitable for kinetic analysis and inhibitor screening." Anal Biochem. 396, 112-6). Briefly, heparanase can cleave the synthetic pentasaccharide Fondaparinux, which is an antithrombotic drug, structurally corresponding to the antithrombin binding site of heparin. After hydrolysis by heparanase, a trisaccharide and a reducing disaccharide are obtained. The latter can be easily quantified in order to assess heparanase activity. In the present examples, the assay solution comprises (100 μl) 40 mM sodium acetate buffer pH 5.0 and 100 mM Fondaparinux (GlaxoSmithKline), with or without inhibitor sample. Heparanase was added to a final concentration of 140 pM at the beginning of the assay. The plates were sealed with adhesive tape and incubated at 37° C. for 2-24 hours. The assay was stopped by addition of 100 μL of a 1.69 mM 4-[3-(4-iodophenyl)-1H-5 tetrazolio]-1,3-benzene disulfonate (WST-1, Aspep, Melbourne, Australia) solution in 0.1M NaOH. The plates were resealed with adhesive tape and developed at 60° C. for 60 minutes. The absorbance was measured at 584 nm (Fluostar, BMG, Labtech). In each plate, a standard curve constructed with D-galactose as the reducing sugar standard was prepared in the same buffer and volume over the concentration range of 2 to 100 uM. The $IC_{50}$ value was determined. Results obtained using the above cited colorimetric assay were validated using a different test that employs an extracellular matrix (ECM) labeled with radioactive sulfate as substrate. Briefly, the ECM substrate is deposited by cultured corneal endothelial cells and hence closely resembles the subendothelial basement membrane in its composition, biological function and barrier properties. Detailed information about the preparation of sulfate labeled ECM and its use for the heparanase assay can be found in: Vlodaysky, I., Current Protocols in Cell Biology, Chapter 10: Unit 10.4, 2001.

In Vivo Testing

The antimyeloma activity in vivo was tested substantially following the procedure described in Yang Y et al. (Yang Y., et al. 2007. "The syndecan-1 heparan sulfate proteoglycan is a viable target for myeloma therapy." Blood 110:2041-2048). Briefly, CB17 scid/scid mice aged 5 to 6 weeks were obtained from Arlan (Indianapolis, Ind.) or Charles River Laboratories (USA). Mice were housed and monitored in the animal facility of the University of Alabama in Birmingham. All experimental procedures and protocols were approved by the Institutional Animal Care and Use Committee. $1 \times 10^6$ heparanase-expressing CAG myeloma cells (high or low expressing) were injected subcutaneously into the left flank of each mouse. 10 days after injection of tumor cells, mice were implanted with Alzet osmotic pumps (Durect Corporation, Cupertino, Calif.) on the right flank. Pumps contained either solution of test compounds (new heparin derivatives) or phosphate buffer (PBS) as control. The solution was delivered continuously for 14 days. After 14 days, the animals were killed and the wet weight of the subcutaneous tumors and the mean sera kappa level were assayed and compared among the experimental groups by log-rank test (p<0.05 was considered statistically significant).

Weekly luciferase bioluminescence imaging provides quantitative data on primary tumors and tracks metastasis within bone as well as soft tissues. Notably, the SCID-hu model is unique in that human tumor cells are injected directly into small pieces of human fetal bone implanted subcutaneously in SCID mice, thus closely recapitulating human myeloma.

General Procedure of NMR Analysis

Spectra were recorded at 25° C. on a Bruker Avance 500 spectrometer (Karlsruhe, Germany) equipped with a 5-mm TCI cryoprobe or with a 10 mm BBO probe. Integration of peak area or volumes in the spectra was made using standard Bruker TopSpin 2.0 software.

N-Desulfation of Unfractionated Heparin

Example 1 (G8220)

UFH (4.01 g, lot. G3378) was dissolved in water (32 ml) and treated under stirring with Amberlite IR 120 (H+, 144 ml). The filtered acid solution was brought to pH 7 with pyridine, then concentrated to dryness under reduced pressure. The resulting pyridinium salt was dissolved in 40 ml of a mixture of DMSO:$H_2O$ (95:5 by volume), then stirred at 25° C. for 48 h. After dilution with 40 ml of water, the solution was dialyzed at 4° C. for 16 hours against distilled water in membrane (cut-off: 3,500 Da). Concentration under reduced pressure and lyophilization gave: G8220 (2.7 g), yield=67% w/w, MW=19,100 Da, N-desulfation degree determined by $^{13}$C-NMR=74.7% of the total glucosamine residues, 2-O sulfated uronic acid determined by $^{13}$C-NMR=18% of the total monosaccharides.

Example 2 (G8343)

Following the procedure described in Example 1, a sample of UFH (0.25 g, lot. G3378) was converted in the corresponding pyridinium salt, which was N-desulfated in a mixture of DMSO:MeOH (95:5 by volume). After 2 hours under stirring at 25° C., reaction mixture was processed, following the same final procedure described in Example 1, to give G8343 (0.172 g), yield=69% w/w, MW=18,000 Da, N-desulfation degree determined by $^{13}$C-NMR=63.3% of the total glucosamine residues, 2-O sulfated uronic acid determined by $^{13}$C-NMR=19% of the total monosaccharides.

Example 3 (G8516)

Starting from a sample of UFH (0.25 g, lot G3378) and following the procedure described in Example 2, but reducing to 40 minutes the N-desulfation reaction time, G8516 was obtained (0.17 g), yield=68%, N-desulfation degree by $^{13}$C-NMR=49.7% of the total glucosamine residues, 2-O sulfated uronic acid determined by $^{13}$C-NMR=17% of the total monosaccha rides.

Example 4 (G8147)

UFH (2.5 g, lot. G3378) was dissolved in water (20 ml) and treated under stirring with Amberlite IR 120 (H+, 90 ml). The filtered acid solution was brought to pH 7 with pyridine, then concentrated to dryness under reduced pressure. The resulting pyridinium salt was dissolved in 25 ml of a mixture of DMSO: MeOH (90:10 by volume), then stirred at 25° C. for 18 hours. After dilution with 25 ml of water, the solution was dialyzed at 4° C. for 16 hours against distilled water in membrane (cut-off: 3,500 Da). Concentration under reduced pressure and lyophilization gave: G8147 (1.9 g), yield=76% w/w, MW=18,200 Da, N-desulfation degree by $^{13}$C-NMR=60% of the total glucosamine residues.

Example 5 (G9416)

UFH (5 g, lot. G3378) was dissolved in water (40 ml) and treated under stirring with Amberlite IR 120 (H+, 90 ml). The filtered acid solution was brought to pH 7 with pyridine, then concentrated to dryness under reduced pressure. The resulting pyridinium salt was dissolved in 100 ml of a mixture of DMSO: MeOH (95:5 by volume), then stirred at 25° C. for 18 hours. After dilution with 100 ml of water, the solution was dialyzed at 4° C. for 16 hours against distilled water in membrane (cut-off: 3,500 Da). Concentration under reduced pressure and lyophilization gave: G9416 (3.65 g), yield=73% w/w, MW=18,800 Da, N-desulfation degree by $^{13}$C-NMR=77% of the total glucosamine residues.

Example 6 (G8079)

UFH (1 g, lot. G3378) was dissolved in water (8 ml) and treated under stirring with Amberlite IR 120 (H+, 90 ml) for 30 minutes. The filtered acid solution was brought to pH 7 with pyridine, then concentrated to dryness under reduced pressure. The resulting pyridinium salt was dissolved in 10 ml of a mixture of DMSO:MeOH (95:5 by volume), then stirred at 25° C. for 16 hours. After dilution with 10 ml of water, the solution was dialyzed at 4° C. for 3 days against distilled water in membrane (cut-off: 3,500 Da). Concentration under reduced pressure and lyophilization gave: G8079 (1 g), yield=100% w/w, N-desulfation degree by $^{13}$C-NMR=60% of the total glucosamine residues.

Periodate Oxidation and Sodium Borohydride Reduction of N-Desulfated Heparins

Example 7 (G8340)

A sample of G8220 of example 1 (0.25 g, 74.7% of N-desulfated heparin residues), dissolved in water (7.3 ml) and cooled to 4° C., was added to an equal volume of 0.2 M $NaIO_4$. The pH value was adjusted to 6.8 with 2M $NaHCO_3$ (about 2.1 ml) and, under stirring in the dark at 4° C., 0.08 M nitrilotriacetic acid (NTA, 10 ml) was added to the solution. The pH value from 4.0 was brought to 6.6 by adding 2M NaHCO$_3$ and the reaction mixture was kept under stirring at 4° C. for 8 hours. The excess of periodate was quenched by adding ethylene glycol (0.73 ml); after 1 hour the reaction mixture was desalted by dialysis against distilled water in membrane (cut-off: 3,500 Da) at 4° C. for 16 hours. The desalted solution was treated with NaBH$_4$ (0.164 g, 3.4 mmoles), stirred for 3 hours at 25° C., then its pH value was brought to 4 with 1N HCl for quenching the NaBH$_4$ excess, and after a 10 minutes stirring, neutralized with 0.1 N NaOH. After dialysis against distilled water at 4° C. for 16 hours in membrane (cut-off: 3,500 Da), concentration under reduced pressure and freeze drying, 0.202 g of G8340 was obtained, yield=90% w/w, MW=8,400 Da. The percentages, over the total of monosaccharide residues, of RO (53%), IdoA2S (35%), GlcNAc (9%) and GlcNH$_2$ (12%) were determined by $^{13}$C-NMR.

In vitro heparanase inhibition: IC$_{50}$=20 ng/ml.

In vivo antimyeloma activity: 60 mg/Kg/day for 14 days: 75% tumor inhibition and 60% serum K inhibition.

Example 8 (G8438)

Starting from G8343 of Example 2 (0.171 g of 63.3% of N-desulfated heparin residues) and following the same procedure described in Example 7, G8438 was obtained (91.4 mg), yield=82%, MW=6,800 Da. The percentages of RO (38%), IdoA2S (32%), GlcNAc (8%), GlcNH$_2$ (4%), were determined by $^{13}$C-NMR.

In vitro heparanase inhibition IC$_{50}$: 60 ng/ml.

Example 9 (G8588)

Starting from G8516 of Example 3 (0.171 g of 44% of N-desulfated heparin residues) and following the procedure described in Example 7, G8588 (0.136 g) was obtained, yield=80%, MW=11,000 Da, the percentages of GlcNAc (30%), GlcNH$_2$ (13%), IdoA2S (34%) RO (37%) were determined by $^{13}$C-NMR.

Example 10 (G9578)

Starting from G9416 of example 5, following the procedure described in Example 7, G9578 was obtained, yield=89%, MW=6,300 Da, N-desulfation degree by $^{13}$C-NMR=48% of the total glucosamine residues. The percentages of RO (45%) and IdoA2S (35%) over the total residues of glycosaminoglycan were determined by $^{13}$C-NMR. In vitro and in vivo testing on the inventive product yielded the following results:

In vitro heparanase inhibition: IC$_{50}$=75 ng/ml;

in vivo antimyeloma activity (60 mg/kg day for 14 days): 63% tumor inhibition.

Example 11 (G8188)

A sample of N-desulfated heparin G8147 of example 4 (0.25 g, 60% N-desulfated heparin residues), dissolved in water (7.3 ml) and cooled to 4° C., was added to an equal volume of 0.2 M NaIO$_4$. The pH value was adjusted to 6.8 with 2M NaHCO$_3$ (about 2.1 ml), under stirring in the dark at 4° C. for 16 hours. The excess of periodate was quenched by adding ethylene glycol (0.73 ml) and after 1 hour the reaction mixture was desalted by dialysis against distilled water in membrane (cut-off: 3,500 Da) at 4° C. for 16 hours. The desalted solution was treated with NaBH$_4$ (0.164 g, 3.4 mmoles), stirred for 3 hours at 25° C., then its pH value was brought to 4 with 1N HCl for quenching the NaBH$_4$ excess and, after a 10 minutes stirring, it was neutralized with 0.1 N NaOH. After dialysis against distilled water at 4° C. for 16 hours in membrane (cut-off: 3,500 Da), concentration under reduced pressure and freeze drying, 0.168 g of G8188 was obtained, yield=67% w/w, MW=3,460 Da. The percentages of RO (43%), IdoA2S (40%), GlcNAc (6%) and GlcNH$_2$ (4%) were determined by $^{13}$C-NMR.

Example 12 (G8189)

A sample of G8147 (0.25 g, 60% of N-desulfated heparin residues), dissolved in water (7.3 ml) and cooled to 4° C., was added to an equal volume of 0.2 M NaIO$_4$. The pH value was adjusted to 6.8 with pyridine (5% v/v, about 730 µl), under stirring in the dark at 4° C. for 16 hours. The excess of periodate was quenched by adding ethylene glycol (0.73 ml) and after 1 hour the reaction mixture was desalted by dialysis against distilled water in membrane (cut-off: 3,500 Da) at 4° C. for 16 hours. The desalted solution was treated with NaBH$_4$ (0.164 g, 3.4 mmoles), stirred for 3 hours at 25° C., then its pH value was brought to 4 with 1N HCl for quenching the NaBH$_4$ excess and, after a 10 minutes stirring, neutralized with 0.1N NaOH. After dialysis against distilled water at 4° C. for 16 hours in membrane (cut-off: 3,500 Da), concentration under reduced pressure and freeze drying, 0.181 g of G8189 was obtained, yield=72% w/w, MW=5,150 Da. The percentages of RO (49%), IdoA2S (39%), GlcNAc (7%) and GlcNH$_2$ (7%) were determined by $^{13}$C-NMR.

Example 13 (G8217)

A sample of G8147 (0.25 g, 60% of N-desulfated heparin residues), dissolved in water (7.3 ml) and cooled to 4° C., was added to an equal volume of 0.2 M NaIO$_4$. The pH value was adjusted to 6.8 with 2M NaHCO$_3$ (about 2.1 ml) and 30 ml of MnCl$_2$ 0.05M (the final concentration in the solution was 0.00001 M) were added under stirring in the dark at 4° C. for 16 hours. The excess of periodate was quenched by adding ethylene glycol (0.73 ml). During the night, the sample precipitated because the pH became 8 then its pH value was brought to 6 with 1N HCl. After 1 hour the reaction mixture was desalted by dialysis against distilled water in membrane (cut-off: 3,500 Da) at 4° C. for 16 hours. The desalted solution was treated with NaBH$_4$ (0.164 g, 3.4 mmoles), stirred for 3 hours at 25° C., then its pH value was brought to 4 with 1N HCl for quenching the NaBH$_4$ excess and after a 10 minutes stirring, neutralized with 0.1N NaOH. After dialysis against distilled water at 4° C. for 16 hours in membrane (cut-off: 3,500 Da), concentration under reduced pressure and freeze drying, 0.230 g of G8217 was obtained, yield=92% w/w, MW=7,455 Da. The percentages of RO (31%), IdoA2S (29%), GlcNAc (8%) and GlcNH$_2$ (6%) on the total of glycosaminoglycan residues were determined by $^{13}$C-NMR.

Example 14 (G8219)

A sample of G8147 (0.25 g, 60% of N-desulfated heparin residues), dissolved in water (7.3 ml) and cooled to 4° C., was added to an equal volume of 0.2 M NaIO$_4$. The pH value was adjusted to 6.8 with 2M NaHCO$_3$ (about 1.2 ml) and, under stirring in the dark at 4° C., 0.08M nitrilotriacetic acid (NTA, 10 ml) and 31 ml of MnCl$_2$ 0.05M were added to the solution. The pH value was brought from 4.0 to 6.3 by adding 2M NaHCO$_3$ and the reaction mixture was kept under stirring at 4° C. for 8 hours. The excess of periodate was quenched by adding ethylene glycol (0.73 ml) and after 1 hr the reaction mixture was desalted by dialysis against distilled water in membrane (cut-off: 3,500 Da) at 4° C. for 16 hours. The dialyzed solution was treated with NaBH$_4$ (0.164 g, 3.4 mmoles), stirred for 3 hours at 25° C., then its pH value was brought to 4 with 1N HCl for quenching the NaBH$_4$ excess, and after a 10 minutes stirring, neutralized with 0.1N NaOH. After dialysis against distilled water at 4° C. for 16 hours in membrane (cut-off: 3,500 Da), concentration under reduced pressure and freeze drying, 0.202 g of G8219 was obtained, yield=90% w/w, MW=7,330 Da. The percentages of RO (54%), IdoA2S (36%), GlcNAc (9%) and GlcNH$_2$ (8%) were determined by $^{13}$C-NMR.

Comparative Example 15 (G8092)

To a sample of G8079 (1 g, N-desulfated heparin), dissolved in water (29.2 ml) and cooled to 4° C., an equal volume of NaIO$_4$ (pH$_5$) was added and the reaction mixture was kept under stirring at 4° C. for 8 hours. The excess of periodate was quenched by adding ethylene glycol (2.9 ml) and after 1 hour the reaction mixture was desalted by dialysis against distilled water in membrane (cut-off: 3,500 Da) at 4° C. for 16 hours. The dialyzed solution was treated with NaBH$_4$ (0.657 g, 3.4 mmoles), stirred for 3 hours at 25° C., then its pH value was brought to 4 with 1N HCl for quenching the NaBH$_4$ excess, and after a 10 minutes stirring, neutralized with 0.1N NaOH. After dialysis against distilled water at 4° C. for 72 hours in membrane (cut-off: 3,500 Da), concentration under reduced pressure and freeze drying, 0.643 g of G8092 was obtained, yield=64% w/w, MW=6,064 Da. The $^{13}$C-NMR analysis shows a peak at 95 ppm of N-desulfated glucosamine. The oxidation reaction at acidic pH does not occur.

The invention claimed is:

1. A process for the preparation of a glycosaminoglycan derivative inhibiting heparanase, consisting essentially of:
   a) N-desulfation of from 25% to 100% of the N-sulfated glucosamine residues of a glycosaminoglycan;
   b) oxidation of from 25% to 100% of the 2-N-, 3-O-non-sulfated glucosamine residues and of the 2-O-non-sulfated uronic acid residues of said glycosaminoglycan of step a), under conditions effective to convert adjacent diols and adjacent OH/NH$_2$ to aldehydes;
   c) reduction of said oxidized glycosaminoglycan, under conditions effective to convert said aldehydes to alcohols;
   wherein the glycosaminoglycan is a natural or synthetic glycosaminoglycan, and wherein the natural or synthetic glycosaminoglycan is heparin, low-molecular-weight heparin, heparin sulfate, or fractions thereof.

2. The process of claim 1, wherein the oxidation in step b) is by periodate at a pH of from 5.5 to 10.0.

3. The process of claim 1, wherein the reduction in step c) is by sodium borohydride.

4. The process of claim 1, wherein the natural or synthetic glycosaminoglycan is unfractionated heparin or heparin having a molecular weight of from 3,500 to 8,000 Da.

* * * * *